United States Patent [19]

Selander

[11] Patent Number: 4,644,163

[45] Date of Patent: Feb. 17, 1987

[54] MATERIAL IDENTIFICATION USING INFRARED THERMOMETRY

[75] Inventor: Raymond K. Selander, Hopewell Junction, N.Y.

[73] Assignee: International Business Machines Corporation, Armonk, N.Y.

[21] Appl. No.: 787,866

[22] Filed: Oct. 16, 1985

Related U.S. Application Data

[63] Continuation of Ser. No. 404,008, Aug. 2, 1982, abandoned.

[51] Int. Cl.$^4$ .......................... B07C 5/34; G01N 21/47
[52] U.S. Cl. .................................. 250/341; 250/358.1; 209/577; 356/371; 356/446; 356/448
[58] Field of Search ............... 250/339, 341, 559, 340, 250/358.1, 359.1, 571; 209/577, 587, 700; 356/446, 445, 448, 371, 237

[56] References Cited

U.S. PATENT DOCUMENTS

| | | | |
|---|---|---|---|
| 3,747,755 | 7/1973 | Senturia et al. | 250/339 |
| 3,850,526 | 11/1974 | Corey, III | 356/445 |
| 4,124,803 | 11/1978 | Bowers | 250/559 |
| 4,236,640 | 12/1980 | Knight | 250/365 |
| 4,262,806 | 4/1981 | Drabs | 250/223 R |

FOREIGN PATENT DOCUMENTS 2057123  3/1981  United Kingdom ............... 250/341

Primary Examiner—Carolyn E. Fields
Attorney, Agent, or Firm—Wolmar J. Stoffel

[57] ABSTRACT

Automatic material identification is achieved using infrared thermometry. A focused beam of high flux energy is passed through a dichroic beam-splitter to remove visible UV with the remaining infrared directed to the surface of the material to be identified. An infrared thermometer sensor is positioned to sense the magnitude of the energy received from the material surface with the magnitude of the energy being indicative of the type of material scattering such energy. Control apparatus are employed to provide control signals as a function of the type of material identified such that automatic process operations may be effected in accordance therewith.

13 Claims, 5 Drawing Figures

CERAMIC
GREEN SHEET

PAPER

PLASTIC

MATERIAL IDENTIFICATION USING INFRARED THERMOMETRY

This application is a continuation of U.S. Ser. No. 404,008, filed Aug. 2, 1982, now abandoned.

BACKGROUND OF THE INVENTION

1. Field of the Invention

The subject invention relates to material identification and, more particularly, to material identification using infrared thermometry.

2. Description of the Problem and Prior Art

One of the difficulties encountered in automatic material handling apparatus resides in the fact that typically the apparatus is incapable of identifying the type of material being handled. Inability to distinguish one type of material from another imposes a constraint on the effectiveness of such apparatus since in many applications it is not always completely predictable what type of material will be presented for the next operation. This is particularly true in the use of robots programmed to carry out a sequence of operations in a fixed pattern without the aid of sensors to identify the material being handled. In such operations, the robot is typically programmed to pick up in succession different type sheet material arranged in a stack for separation and further processing. Where, in such applications, the different types of sheet material are not prearranged in the stack as planned or predicted, the inability of the robot to recognize this fact may result in moving the wrong material to the next operation in the sequence.

On the other hand, in some operations the type of material to be handled through the various sequence of operations is not predictable but rather the material may be any one of several types available in random fashion. In such applications, it is desirable to be able to identify the type of material to be moved so that it may be moved to the appropriate location for the next processing step.

Although sensor systems are known for measuring various parameters of materials during processing, no sensor system is known for identifying the type of material being processed. One parameter typically measured during processing is temperature and one common approach to measuring temperature involves use of infrared thermometry. Although infrared thermometry systems are known to be effective to remotely measure temperature of materials, such systems have, heretofore, not been known to be effective to remotely identify different types of material.

Likewise, although sensors are known to optically sense various conditions of the surface of material, no such system has been known to identify the type of material. An example of a typical sensor system that acts to detect the state or condition of the surface of material may be seen by reference to the article entitled "Fibre-Optic Object Sensor" by F. J. Bealle, IBM Technical Disclosure Bulletin, Vol. 23, No. 5, September 1980, pp. 1384–85. Another example may be seen by reference to Baxter et al in an IBM Technical Disclosure Bulletin article entitled "Reflectance Meter", Vol. 11, No. 5, October 1968, pp. 520–21. A further scheme which relies on optical reflectance from the surface of material is that described by C. R. Strife in the IBM Technical Disclosure Bulletin article entitled "Automatic Core Feed", Vol. 13, No. 6, November 1970, pp. 1633–34.

Although these optical reflectance schemes are effective for measuring the condition of the surface of the material, such schemes are ineffective for identifying the type of material being employed. One of the reasons why optical reflectance schemes are not effective to identify the type of material from which the reflection occurs is that optical reflection is not a function of material characteristics indicative of the type of material. For example, two materials with a generally white surface, such as ceramic and paper, would generally provide indistinguishable optical reflectance. Thus, the use of reflected light in the visible range is not effective for identifying types of material.

SUMMARY OF THE INVENTION

In accordance with the principles of the present invention, an arrangement is provided for automatically identifying material. More particularly, in accordance with the principles of the present invention, an arrangement is provided for automatically identifying material types using an infrared thermometry system. The infrared thermometry system is arranged to sense heat reflected from the surface of the material to be identified such that the magnitude of the reflected heat is a function of the type of material.

In the material identification thermometry system of the present invention, heat from a halogen or incandescent lamp, for example, is focused upon material to be identified. A dichroic beam-splitter reflects the majority of the visible spectrum from the lamp to a flat black absorbing surface. The heat wavelength signals are permitted to penetrate the filter and are reflected from the surface of the material to be identified to an infrared thermometer sensor. The magnitude of the reflected heat is indicative of the type of material being identified. Such material identification may be employed in any of a variety of applications. For example, such material identification may be employed in conjunction with the automatic handling of material whereby the throughput of such automated systems may be significantly increased.

It is, therefore, an object of the present invention to provide a system for automatically identifying material types.

It is a further object of the present invention to provide a system for the automatic identification of material types using infrared thermometry.

It is yet a further object of the present invention to provide a system for automatically identifying material types selected from a variety of materials.

It is yet still a further object of the present invention to provide a system for automatically identifying material types which identification may be employed to facilitate the automatic handling of such material.

The foregoing and other objects, features and advantages of the invention will be apparent from the following more particular description of the preferred embodiments of the invention, as illustrated in the accompanying drawings.

DETAILED DESCRIPTION OF THE PREFERRED EMBODIMENT

Figure 1:
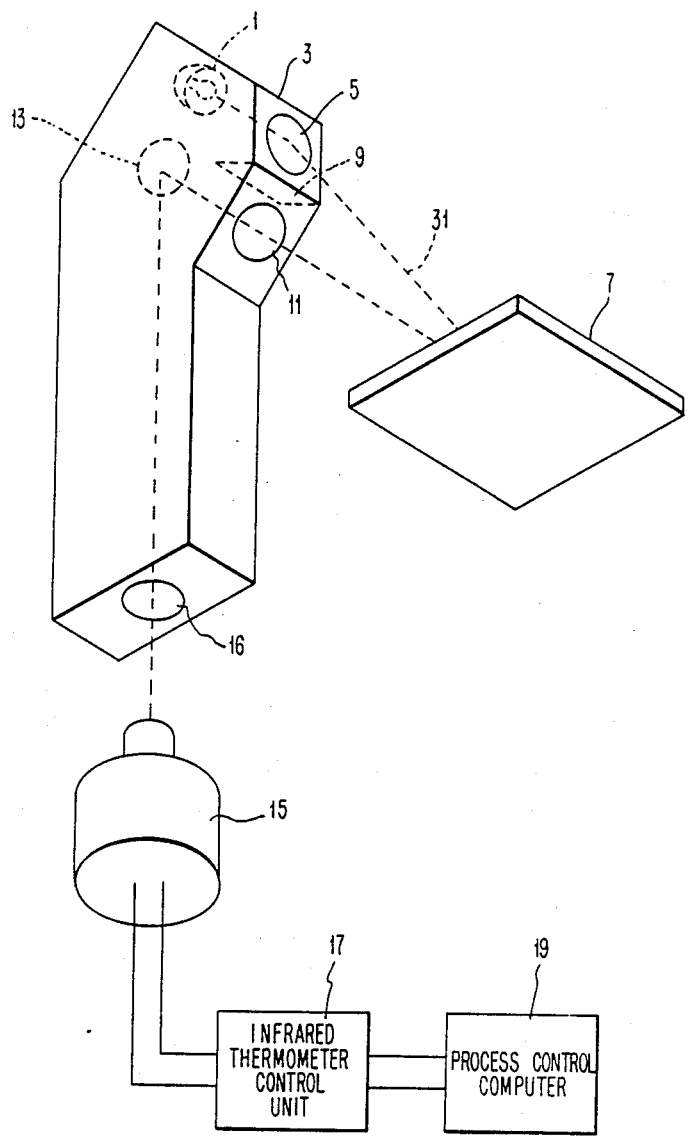
FIG. 1 shows the infrared thermometry sensor system for the automatic identification of materials, in accordance with the present invention.

In the sensor system arrangement shown in FIG. 1, a halogen lamp 1 is employed, within housing 3, as a heat source. In this regard, a conventional 150 watt DZE halogen lamp has been found effective. However, a conventional incandescent lamp has been found to also be adequate. Other lamps may also work so long as they provide a sufficiently high flux in the spectral range required, i.e., 2.0 to 2.6 microns.

The heat from lamp 1 is focused through dichroic beam-splitter 5 upon the surface of the material 7 to be identified. Typically, the heat may be focused to a one-inch diameter spot on the surface of the material. Dichroic beam-splitter 5, which will be shown in more detail in FIG. 2, acts to reflect the majority of the visible spectrum emanating from lamp 1 to light absorber 9. Light absorber 9 comprises a flat black absorbing surface within the sensor housing. As is understood by those skilled in the art, the beam-splitter acts to reflect the ultraviolet visible at an angle of 90° with respect to the incident light. By such an arrangement, the harmful ultraviolet light is absorbed by the absorbing surface. On the other hand, the heat wavelength signals are permitted to penetrate filter 5 and are focused on the surface of material 7. In this regard, the infrared light passing through beam-splitter 5 includes a small percentage of red visible light to aid in the optical alignment of the system.

The light reflected from the surface of material 7 is passed through hole 11 to mirror 13 where it is reflected to infrared thermometer sensor 15 through hole 16. Infrared thermometer sensor 15 may be any of a variety of commercially available general purpose infrared thermometers which respond within the 2.0 to 2.6 micron wavelengths. Typically, the temperature span for such sensors ranges from 150° to 1400° F. An example of such a sensor is the IRCON series 6000 infrared thermometer sensor.

The signal from infrared thermometer sensor 15 is passed to infrared thermometer control unit 17 which acts to respond to the magnitude of the reflected signal sensed by sensor 15. Control unit 17 may be arranged to provide a visual indication of the percentage of infrared reflection from the surface of material 7. In addition, control unit 17 acts to provide control signals to process control computer 19 in accordance with the magnitude of the reflected signals. In this regard, control unit 17 has a plurality of predetermined thresholds which act to provide the appropriate trigger levels at which control signals are to be sent to process control computer 19. Process control computer 19 may be used to control any of a variety of process operations. Typically, one of these operations would involve control of a robot to handle material, such as sheet material 7 in FIG. 1. For example, sheet material 7 may be one of a plurality of stacked sheets of material which are unstacked by the robot and moved to an appropriate position for the next process step, such as an inspection operation. The stack of material may comprise alternate types of material which require movement to different points in accordance with the material type. For example, the stack may comprise alternate sheets of ceramic greensheet and paper positioned in a plastic tray.

Figure 2:
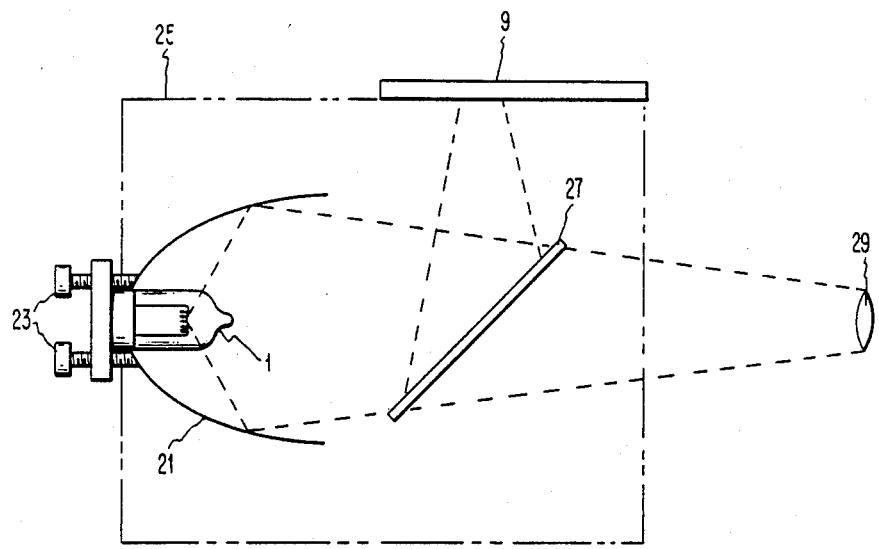
FIG. 2 shows the dichroic beam-splitter for filtering UV visible light from the light source employed in FIG. 1.

In the dichroic beam-splitter filter arrangement shown in FIG. 2, lamp 1 is focused by elliptical reflector 21 in response to adjustment to the focus range effected by knobs 23, mounted on enclosure 25. Infrared dichroic beam-splitter 27 acts to split the visible flux from high flux light source 1 to absorber plate 9. Absorber plate 9 may be coated with an optically flat black paint for effective absorption. The infrared flux is passed to target plane 29 which, in the embodiment shown in FIG. 1, comprises the surface of the material to be identified.

In operation, light source 1 acts to provide a focused source of infrared energy to the surface of material 7. The reflected infrared energy from the surface of material 7 is passed to mirror 13 and then to infrared thermometer sensor 15. Infrared thermometer sensor 15 measures the amount of reflection from the surface of material 7 with the signal strength from sensor 15 being indicative of the material being identified. Spectral content is limited in conventional fashion to the region of 2.0 to 2.6 microns by an optical filter in the convergence column of the sensor 15. The signal from the sensing element within sensor 15, varying in amplitude proportionally to the intensity of the incoming radiation, is amplified and then demodulated therein to a DC voltage which is transmitted to control unit 17. The control unit acts to amplify the signal from sensor 15 and then linearizes the amplified signal so that the output signal from the amplifiers is a +10.0 volt DC full scale analog signal directly proportional to temperature. This analog output is used to trigger the threshold circuits within control unit 17 to provide appropriate output control signals at the desired magnitude of the analog signal. It should be appreciated, in this regard, that monitor control unit 17 may comprise any of the variety of commercially available control units, such as the IRCON series 6000 infrared thermometer control unit instrument.

It has been found that the percentage of reflected heat may vary markedly with the type of material upon which the incident infrared is focused. The difference in physical properties, such as composition and texture, act to provide this marked difference. For example, ceramic greensheet material provides a reflected signal of 50% of the incident signal while paper provides a reflected signal of 20%. On the other hand, plastic only provides a reflected signal of 2% of the incident signal. With such differences, the thresholds in control unit 17 may be set at the reflection mid points, for example 11% for point 1 and 35% for point 2. In this regard, although ceramic and paper are white in color, it is the physical characteristics of these materials that act to determine the magnitude of the reflected signal. The ceramic surface, being very coarse and hard, apparently acts to reflect in scattered fashion a substantial portion of the incident infrared energy. On the other hand, paper being relatively smooth and soft, appears to absorb more and scatter less of the reflected energy than the ceramic. In this regard, it would seem that the smoothness of the paper tends to cause a greater percentage of the incident energy to reflect, in focused fashion, along a line at the same angle with respect to the surface as the angle of incident light.

Figure 3A:
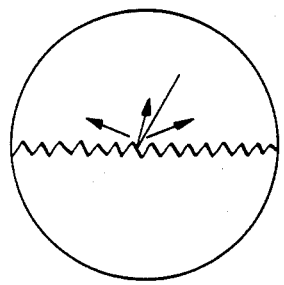
FIGS. 3A–3C show enlarged cross-sections of the surface of three different types of material identified using the sensor system shown in FIG. 1.
Figure 3B:
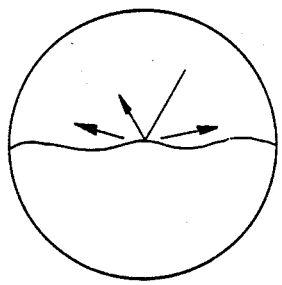
Figure 3C:
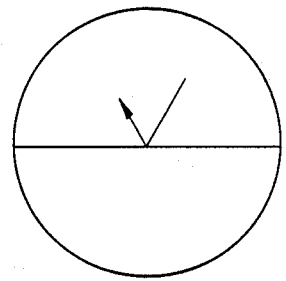

It appears that very little of the reflected energy from the surface of plastic is sensed by sensor 15 due to the fact that plastic is quite smooth and hard thereby causing an even greater percentage of the reflected energy to follow, in focused fashion, the line of the angle of incident energy. FIG. 3 depicts symbolically the action at the surface of these three materials. As can be seen in FIG. 3A, the hardness and roughness of the ceramic greensheet surface acts to scatter the energy radially in somewhat uniform fashion. The paper surface in FIG. 3B acts to cause a significant portion of the incident energy to be reflected along a line at an angle corresponding to the angle of the incident energy. However, some energy is reflected in scattered fashion and it is this scattered energy that is detected by the infrared thermometer sensor. Finally, the hard smooth surface of the plastic shown in FIG. 3C acts to cause a substantial portion of the incident energy to be reflected in focused fashion along a line of reflectance corresponding to the angle of incidence such that the infrared thermometer sensor detects very little of the reflected heat.

The angle of incidence of the infrared energy is not critical. However, as is evident, in accordance with the preferred embodiment, the infrared sensor cannot be placed along the line of reflection since such location would permit the sensor to sense reflected light such that discrimination between materials, according to the described scheme, would not be possible. Accordingly, the infrared sensor should be positioned away from the line of reflection having an angle corresponding to the angle of incidence. For example, the heat source may be positioned at an angle of 60° with respect to the material surface while the infrared sensor may be positioned at an angle of 30° with respect to the material. However, it has been found that the system works well over a wide range of displacements so long as the sensor is not along the line of the angle of reflection corresponding to the angle of incidence.

As an alternative embodiment, it should be appreciated that the infrared sensor may be positioned on the line of reflection at an angle with respect to the surface of the material corresponding to the angle of incidence of the focused infrared beam on said material with such an arrangement providing results which range inversely to those obtained in the preferred embodiment. With such an arrangement, plastic material, for example, would provide a high percentage reflection since most of the reflected heat would go to the sensor while paper would provide the next highest percentage of reflection. The ceramic greensheet material would scatter a large percentage of the heat and, therefore, would provide the lowest percentage reflection to the sensor for these particular examples.

It is clear that materials other than ceramic, paper and plastic may be identified. In this regard, the number of different material types capable of being detected in any one application is limited by material properties which present indiscernible differences in reflection characteristics such that ambiguity would exist.

While the invention has been particularly shown and described with reference to the preferred embodiments thereof, it will be understood by those skilled in the art that various changes in form and details may be made therein without departing from the spirit and scope of the invention.

What is claimed is:

1. A method for identifying paper or plastic sheet material from green ceramic material comprising the steps of;

focusing a beam of infrared energy upon the surface of the materials to be identified from a preselected angle of incidence;

sensing the radiant heat energy scattered from said surface at infrared wavelengths between 2.0 and 2.6 microns, said sensing of heat energy accomplished with a sensor positioned away from the angle of reflectance relative to said angle of incidence;

determining the amount of scattered energy received from said surface through said step of sensing with the amount of energy sensed being a function of the product of the amount of energy radiated by said beam and a constant representative of the physical characteristics of said material; and using the amount of energy scattered from said surface as an indication of the type of material upon which said beam is focused by comparing said amount of energy with known amounts of energy predetermined for similarly scattered energy, which amounts respectively correlate to given material types.

2. The method as set forth in claim 1 wherein said step of focusing a beam of infrared energy comprises focusing a high flux halogen lamp.

3. The method as set forth in claim 2 including the step of filtering UV from said halogen lamp.

4. The method as set forth in claim 3 wherein said step of sensing radiant heat comprises sensing the temperature of said radiant heat with an infrared sensor.

5. The method as set forth in claim 4 wherein said step of using the amount of energy scattered from said surface comprises comparting the amount of energy received from said surface with specific reflectance values indicative of particular materials such that comparison provides identification of the material to be identified.

6. The method as set forth in claim 1 wherein said step of focusing a beam of infrared energy comprises focusing a high flux incandescent lamp.

7. A system for automatically identifying paper or plastic sheet material from ceramic material comprising;

means to provide a focused beam of infrared energy directed from a given angle of incidence at the surface of the material to be identified;

means to sense the radiant heat energy scattered from said surface at infrared wavelengths between 2.0 and 2.6 microns said means to sense radiation positioned to receive radiant heat energy from an angle away from the said angle of incidence;

means for determining the amount of said heat energy sensed by said means to sense with the amount of energy sensed being a function of the product of the amount of energy radiated by said beam and a constant representative of the physical characteristics of said material; and means for comparing the amount of energy sensed with known amounts of energy predetermined for similarly scattered energy, from paper, plastic, or ceramic material, which amounts respectively correlate to given material types.

8. The system as set forth in claim 7 wherein said means to provide a focused beam of infrared energy upon said surface includes a high flux halogen lamp and ellipsoidal reflector.

9. The system as set forth in claim 8 wherein said means to provide a focused beam of infrared energy upon said surface further includes means to filter UV from said halogen lamp.

10. The system as set forth in claim 9 wherein said means to sense radiant heat scattered reflected from said surface comprises an infrared sensor thermometer.

11. The system as set forth in claim 8 wherein said means to provide a focused beam of infrared energy upon said surface includes a high flux incandescent lamp and ellipsoidal reflector.

12. The system as set forth in claim 10 wherein said means responsive to the amount of said heat scattered from said surface includes threshold means responsive to the magnitude of said heat scattered from said surface to provide an output indication indicative of the type of material to be identified.

13. The system as set forth in claim 12 wherein said output indication is used to control the automatic processing of said material in accordance with the type of material.

* * * * *